United States Patent
Li et al.

(10) Patent No.: US 7,064,829 B2
(45) Date of Patent: Jun. 20, 2006

(54) GENERIC INTERFACE FOR AN OPTICAL METROLOGY SYSTEM

(75) Inventors: Shifang Li, Pleasanton, CA (US); Junwei Bao, Santa Clara, CA (US); Nickhil Jakatdar, Los Altos, CA (US); Xinhui Niu, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 265 days.

(21) Appl. No.: 10/394,327

(22) Filed: Mar. 20, 2003

(65) Prior Publication Data

US 2004/0184035 A1  Sep. 23, 2004

(51) Int. Cl.
  *G01J 4/00*  (2006.01)
  *G01B 11/24*  (2006.01)
  *G01B 11/14*  (2006.01)
  *G01B 15/00*  (2006.01)
  *G01N 21/86*  (2006.01)

(52) U.S. Cl. ............. 356/369; 356/601; 356/625; 250/559.19; 250/559.22; 702/155

(58) Field of Classification Search ........ 356/364, 356/369, 630, 2, 388–398, 625–640, 445; 250/225, 559.01–559.07, 559.19–559.24, 250/559.11, 559.26, 559.27; 378/29; 703/2, 703/13; 716/1, 4, 19–21; 438/5, 7–9, 14, 438/16; 700/95, 97, 98, 103, 117–121; 702/81, 702/82, 117, 155–159, 166, 170, 189
See application file for complete search history.

(56) References Cited

U.S. PATENT DOCUMENTS

| | | | |
|---|---|---|---|
| 4,878,179 A * | 10/1989 | Larsen et al. | 716/4 |
| 5,864,633 A | 1/1999 | Opsal et al. | |
| 6,414,302 B1 | 7/2002 | Freeouf | |
| 6,704,661 B1 * | 3/2004 | Opsal et al. | 702/27 |
| 2002/0033954 A1 * | 3/2002 | Niu et al. | 356/601 |
| 2003/0188580 A1 | 10/2003 | Doddi et al. | |

OTHER PUBLICATIONS

PCT International Search Report mailed Mar. 10, 2005 for PCT application PCT/US04/08748, filed Mar. 22, 2004.

* cited by examiner

*Primary Examiner*—Gregory J. Toatley, Jr.
*Assistant Examiner*—Gordon J. Stock, Jr.
(74) *Attorney, Agent, or Firm*—Morrison&Foerster LLP

(57) ABSTRACT

An optical metrology system includes a photometric device with a source configured to generate and direct light onto a structure, and a detector configured to detect light diffracted from the structure and to convert the detected light into a measured diffraction signal. A processing module of the optical metrology system is configured to receive the measured diffraction signal from the detector to analyze the structure. The optical metrology system also includes a generic interface disposed between the photometric device and the processing module. The generic interface is configured to provide the measured diffraction signal to the processing module using a standard set of signal parameters. The standard set of signal parameters includes a reflectance parameter that characterizes the change in intensity of light when reflected on the structure and a polarization parameter that characterizes the change in polarization states of light when reflected on the structure.

29 Claims, 3 Drawing Sheets

GENERIC INTERFACE FOR AN OPTICAL METROLOGY SYSTEM

BACKGROUND

1. Field of the Invention

The present invention relates to wafer metrology, and more particularly to optical metrology.

2. Related Art

Optical metrology involves directing an incident beam at a structure, measuring the resulting diffraction beam, and analyzing the diffraction beam to determine various characteristics, such as the profile of the structure. In semiconductor manufacturing, optical metrology is typically used for quality assurance. For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated.

Optical metrology systems can use various types of photometric devices, which include a light source and a detector capable of detecting the intensity of the diffracted light and converting the light into electrical signals. Conventional photometric devices used in optical metrology systems include reflectometers, which measures the change in the intensity of light, and ellipsometers, which measure the change in the intensity and polarization states of light. Additionally, various types of reflectometers (such as polarized reflectometers, unpolarized reflectometers, and the like) and ellipsometers (such as rotating polarizer ellipsometers (RPEs), rotating compensator ellipsometers (RCEs), phase modulated ellipsometers (PMEs), and the like) can be used.

While these various types of photometric devices convert light into electrical signals, each photometric device can provide the electrical signals as measured diffraction signals using various signal parameters. For example one type of reflectometer can provide measured diffraction signals using different signal parameters than another type of reflectometer. Additionally, two reflectometers that are the same type but made by different manufacturers can provide measured diffraction signals using different signal parameters. Thus, in conventional optical metrology systems, the hardware and software used to analyze the measured diffraction signals received from a photometric device are configured or calibrated to work with the particular photometric device being used, which can be time and cost prohibitive.

SUMMARY

In one exemplary embodiment, an optical metrology system includes a photometric device with a source configured to generate and direct light onto a structure, and a detector configured to detect light diffracted from the structure and to convert the detected light into a measured diffraction signal. A processing module of the optical metrology system is configured to receive the measured diffraction signal from the detector to analyze the structure. The optical metrology system also includes a generic interface disposed between the photometric device and the processing module. The generic interface is configured to provide the measured diffraction signal to the processing module using a standard set of signal parameters. The standard set of signal parameters includes a reflectance parameter that characterizes the change in intensity of light when reflected on the structure and a polarization parameter that characterizes the change in polarization states of light when reflected on the structure.

DESCRIPTION OF DRAWING FIGURES

The present invention can be best understood by reference to the following description taken in conjunction with the accompanying drawing figures, in which like parts may be referred to by like numerals:

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology

Figure 1:
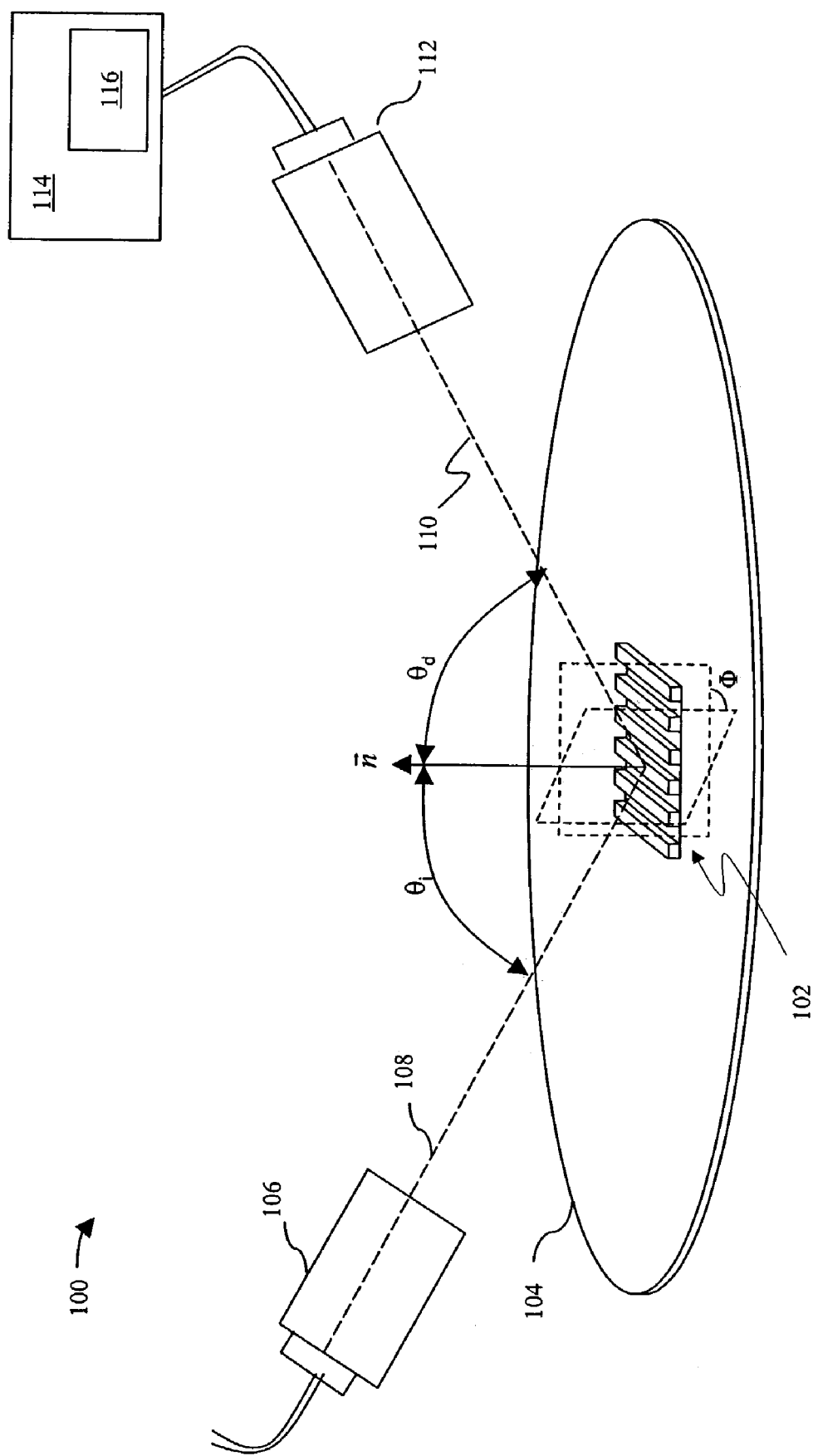
FIG. 1 depicts an exemplary optical metrology system.

With reference to FIG. 1, an optical metrology system 100 can be used to examine and analyze a structure. For example, optical metrology system 100 can be used to determine the profile of a periodic grating 102 formed on wafer 104. As described earlier, periodic grating 102 can be formed in test areas on wafer 104, such as adjacent to a device formed on wafer 104. Alternatively, periodic grating 102 can be formed in an area of the device that does not interfere with the operation of the device or along scribe lines on wafer 104.

As depicted in FIG. 1, optical metrology system 100 can include a photometric device with a source 106 and a detector 112. Periodic grating 102 is illuminated by an incident beam 108 from source 106. In the present exemplary embodiment, incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal $\vec{n}$ and is received by detector 112. Detector 112 converts the diffracted beam 110 into a measured diffraction signal.

To determine the profile of periodic grating 102, optical metrology system 100 includes a processing module 114 configured to receive the measured diffraction signal and analyze the measured diffraction signal. As described below, the profile of periodic grating 102 can then be determined using a library-based process or a regression-based process. Additionally, other linear or non-linear profile extraction techniques are contemplated.

2. Library-Based Process of Determining Profile of Structure

In a library-based process of determining the profile of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, after obtaining a measured diffraction signal, processing module 1114 then compares the measured diffraction signal to simulated diffraction signals stored in a library 116. Each simulated diffraction signal in library 116 can be associated with a hypothetical profile. Thus, when a match is made between the measured diffraction signal and one of the simulated diffraction signals in library 116, the hypothetical profile associated with the matching simulated diffraction signal can be presumed to represent the actual profile of periodic grating 102.

The set of hypothetical profiles stored in library 116 can be generated by characterizing a hypothetical profile using a set of parameters, then varying the set of parameters to generate hypothetical profiles of varying shapes and dimensions. The process of characterizing a profile using a set of parameters can be referred to as parameterizing.

Figure 2A:
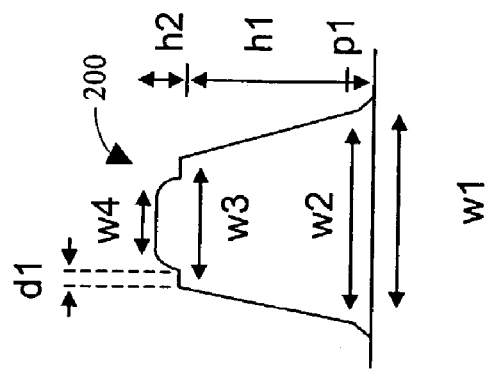
FIGS. 2A–2E depict exemplary profiles of an exemplary periodic grating.
Figure 2B:
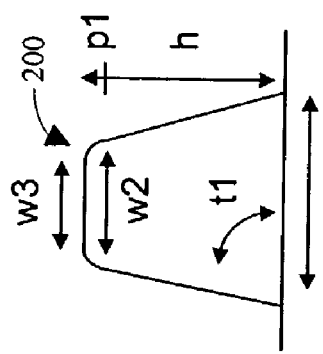
Figure 2C:
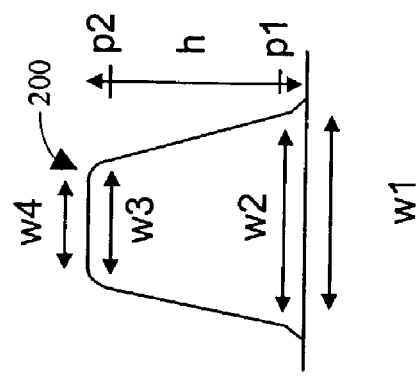
Figure 2D:
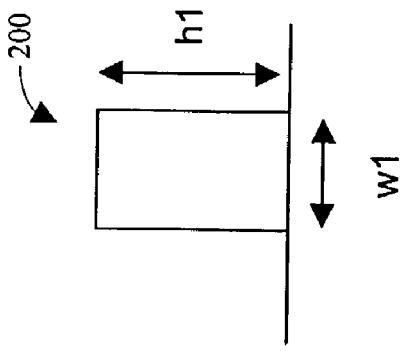
Figure 2E:
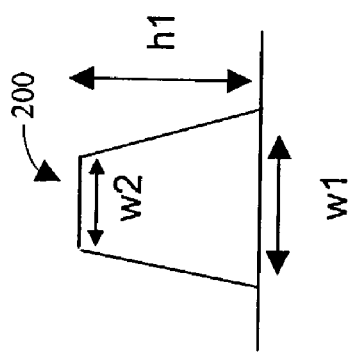

For example, as depicted in FIG. 2A, assume that hypothetical profile 200 can be characterized by parameters h1 and w1 that define its height and width, respectively. As depicted in FIGS. 2B to 2E, additional shapes and features of hypothetical profile 200 can be characterized by increasing the number of parameters. For example, as depicted in FIG. 2B, hypothetical profile 200 can be characterized by parameters h1, w1, and w2 that define its height, bottom width, and top width, respectively. As depicted in FIG. 2C, hypothetical profile 200 can be characterized by parameters h, w1, w2, w3, t1, and p1. As depicted FIG. 2D, hypothetical profile 200 can be characterized by parameters h, w1, w2, w3, w4, p1, and p2. As depicted in FIG. 2E, hypothetical profile 200 can be characterized by parameters h1, h2, w1, w2, w3, w4, p1, and d1. Note that the width of hypothetical profile 200 can be referred to as the critical dimension (CD). For example, in FIG. 2B, parameter w1 and w2 can be described as defining the bottom CD and top CD, respectively, of hypothetical profile 200.

As described above, the set of hypothetical profiles stored in library 116 (FIG. 1) can be generated by varying the parameters that characterize the hypothetical profile. For example, with reference to FIG. 2B, by varying parameters h1, w1, and w2, hypothetical profiles of varying shapes and dimensions can be generated. Note that one, two, or all three parameters can be varied relative to one another.

With reference again to FIG. 1, the number of hypothetical profiles and corresponding simulated diffraction signals in the set of hypothetical profiles and simulated diffraction signals stored in library 116 (i.e., the resolution and/or range of library 116) depends, in part, on the range over which the set of parameters and the increment at which the set of parameters are varied. In one exemplary embodiment, the hypothetical profiles and the simulated diffraction signals stored in library 116 are generated prior to obtaining a measured diffraction signal from an actual structure. Thus, the range and increment (i.e., the range and resolution) used in generating library 116 can be selected based on familiarity with the fabrication process for a structure and what the range of variance is likely to be. The range and/or resolution of library 116 can also be selected based on empirical measures, such as measurements using AFM, X-SEM, and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-Based Process of Determining Profile of Structure

In a regression-based process of determining the profile of a structure, the measured diffraction signal is compared to a simulated diffraction signal (i.e., a trial diffraction signal). The simulated diffraction signal is generated prior to the comparison using a set of parameters (i.e., trial parameters) for a hypothetical profile (i.e., a hypothetical profile). If the measured diffraction signal and the simulated diffraction signal do not match or when the difference of the measured diffraction signal and one of the simulated diffraction signals is not within a preset or matching criterion, another simulated diffraction signal is generated using another set of parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, processing module 114 can generate a simulated diffraction signal for a hypothetical profile, and then compare the measured diffraction signal to the simulated diffraction signal. As described above, if the measured diffraction signal and the simulated diffraction signal do not match or when the difference of the measured diffraction signal and one of the simulated diffraction signals is within a preset or matching criterion, then processing module 114 can iteratively generate another simulated diffraction signal for another hypothetical profile. In one exemplary embodiment, the subsequently generated simulated diffraction signal can be generated using an optimization algorithm, such as global optimization techniques, which includes simulated annealing, and local optimization techniques, which includes steepest descent algorithm.

In one exemplary embodiment, the simulated diffraction signals and hypothetical profiles can be stored in a library 116 (i.e., a dynamic library). The simulated diffraction signals and hypothetical profiles stored in library 116 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Rigorous Coupled Wave Analysis

As described above, simulated diffraction signals are generated to be compared to measured diffraction signals. In one exemplary embodiment, simulated diffraction signals can be generated by applying Maxwell's equations and using a numerical analysis technique to solve Maxwell's equations, such as rigorous coupled-wave analysis (RCWA). It should be noted, however, that various numerical analysis techniques, including variations of RCWA, can be used. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

5. Generic Interface

As noted earlier, with reference again to FIG. 1, optical metrology system 100 can use various types of photometric devices, which can provide measured diffraction signals to processing module 114 using various signal parameters. For example, if the photometric device is a rotating analyzer ellipsometer (RAE), then the measured diffraction signals provided to processing module 114 may include normalized Fourier coefficient parameters such as alpha and beta parameters. Alternatively, if the photometric device is a rotating compensator ellipsometer (RCE), then the measured diffraction signals provided to processing module 114 may include T and A parameters. Examples of alpha and beta parameters and T and A parameters are described in the examples and theory discussed below.

Figure 3:
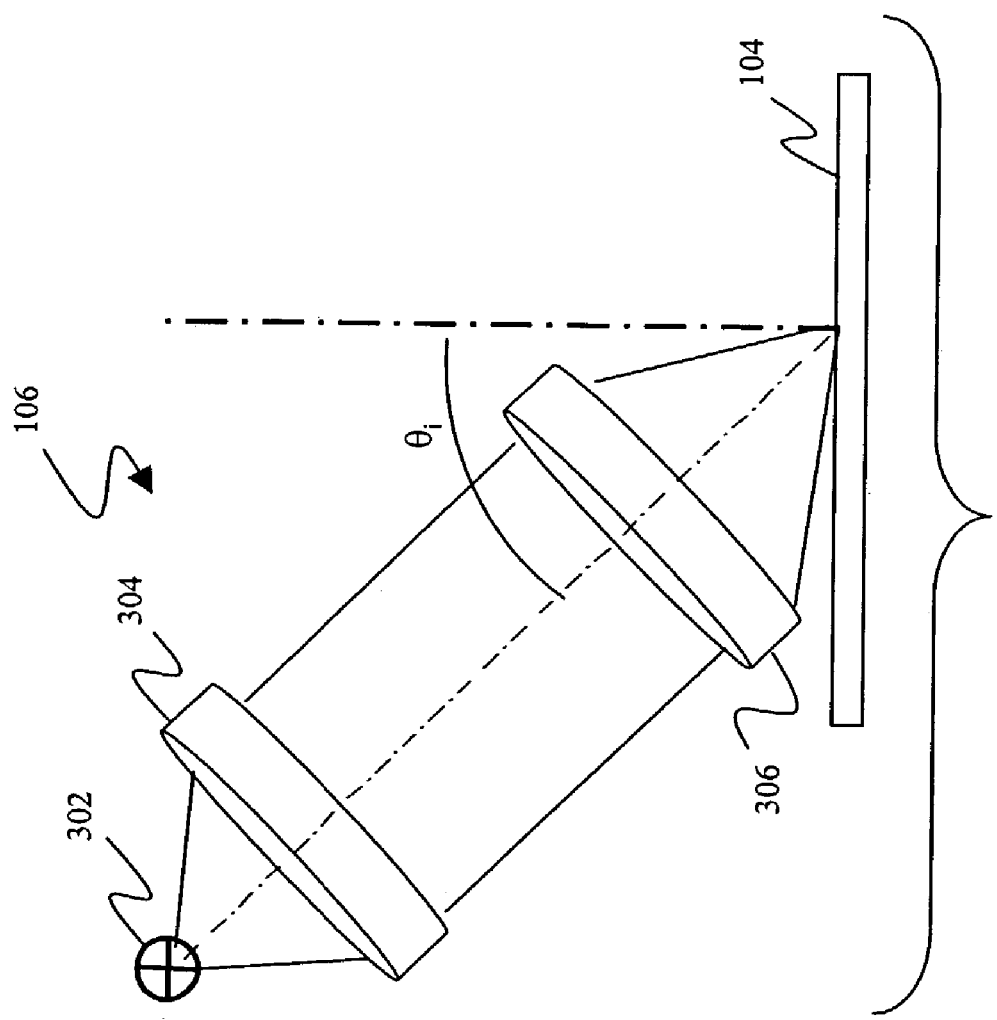
FIG. 3 depicts an exemplary source.

Additionally, in some applications, using certain signal parameters may provide limited or incomplete information to analyze the measured diffraction signals. For example, with reference to FIG. 3, source 106 can include a light source 302, a collimator 304, and a focusing element 306 to focus the beam to form a small spot size. As depicted in FIG. 3, when the beam is focused, the angle of incidence is cone shaped and the $\Psi$ and $\Delta$ are not uniquely defined, as $\Psi$ and $\Delta$ are a function of angle of incidence. Thus, using only the $\Psi$ and $\Delta$ may provide incomplete information to analyze the measured diffraction signals.

Figure 4:
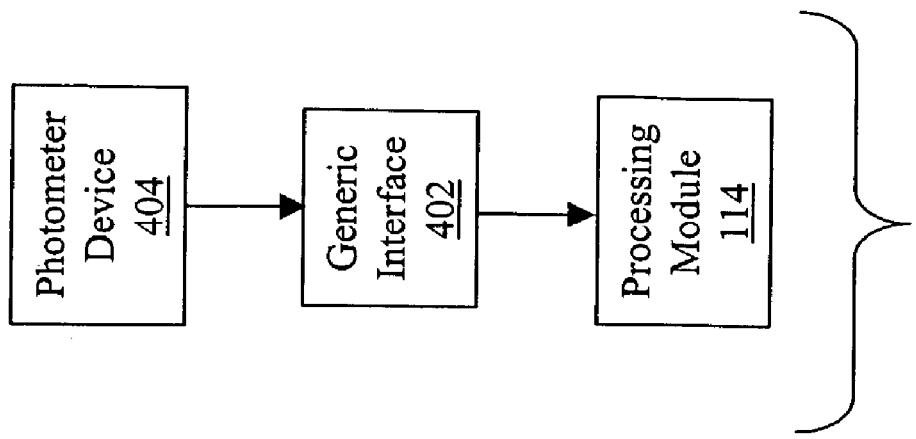
FIG. 4 depicts an exemplary generic interface between a photometric device and a processing module of the exemplary optical metrology system depicted in FIG. 1.

With reference to FIG. 4, in one exemplary embodiment, a generic interface 402 is disposed between a photometric device 404 and processing module 114. Although generic interface 402 is depicted in FIG. 4 as a separate component, it should be recognized that generic interface 402 can be a component of either photometric device 404 or processing module 114. Additionally, generic interface 402 can be implemented in hardware, software, or a combination of hardware and software.

As described above, photometric device 404 includes a source configured to generate and direct light onto a structure, and a detector configured to detect light diffracted from the structure and to convert the detected light into a measured diffraction signal. The processing module is configured to receive the measured diffraction signal from photometric device 404, and more particularly the detector, to analyze the structure, such as determining the profile of the structure.

As also described above, various types of photometric devices 404 can be used, which provide measured diffraction signals using various signal parameters. Thus, in the present exemplary embodiment, generic interface 402 is configured to provide the measured signal to processing module 114 using a standard set of signal parameters. More specifically, the standard set of signal parameters includes a reflectance parameter that characterizes the change in intensity of light when reflected on the structure, and a polarization parameter that characterizes the change in polarization states of light when reflected on the structure.

Thus, when photometric device 404 is a reflectometer that only measures the change in the intensity of light, such as a spectrometer reflectometer, generic interface 402 provides the measured diffraction signal to processing module 114 using only the reflectance parameter of the standard set of signal parameters. When photometric device 404 is an ellipsometer that measures both the change in the intensity of light and polarization states of light, such as a rotating compensator ellipsometer (RCE), generic interface 402 provides the measured diffraction signal to processing module 114 using the reflectance parameter and the polarization parameter of the standard set of signal parameters.

In the present exemplary embodiment, the reflectance parameter (R) of the standard set of signal parameters corresponds to an average of the square of the absolute value of the complex reflection coefficients of the light. The polarization parameter includes a first parameter (N) that characterizes a difference between the square of the absolute value of the complex reflection coefficients normalized to R, a second parameter (S) that characterizes the imaginary component of the interference of the two complex reflection coefficients normalized to R, and a third parameter (C) that characterizes the real component of the interference of the two complex reflection coefficients normalized to R. Thus, the standard set of signal parameters includes the parameters (R, NSC).

When incident light is, for example, 45 degree linear polarized with intensity $I_0$, the parameters (I, N, S, C)×R×$I_0$ correspond to Stokes parameters of the diffracted light. More specifically, when the input Stokes parameters $S_0$, $S_1$, $S_2$, and $S_3$ are $I_0$, 0, $I_0$, and 0, respectively, then the output Stokes parameters $S_0$ corresponds to R×$I_0$, $S_1$ corresponds to negative N×R×$I_0$, $S_2$ corresponds to C×R×$I_0$, and $S_3$ corresponds to negative S×R×$I_0$.

As described above, in one exemplary embodiment, in a library-based process of determining the profile of a structure, the measured diffraction signal is compared to a library of simulated diffraction signals. Thus, in the present exemplary embodiment, the library of simulated diffraction signals is indexed using the standard set of signal parameters (R, NSC). It should be recognized that the simulated diffraction signals in the library can be indexed such that each of the parameters in the standard set of signal parameters are independent. Alternatively, one or more of the parameters can be normalized to one or more of the other parameters in the standard set of signal parameters to reduce the size of the library.

As also described above, in one exemplary embodiment, in a regression-based process of determining the profile of a structure, the measured diffraction signal is compared to a simulated diffraction signal and if the two signals do not match, another simulated diffraction signal is generated. Thus, in the present exemplary embodiment, the simulated diffraction signals can be generated based on the standard set of signal parameters (R, NSC). For example, parameters NSC may be related to tan $\Psi$ and cos $\Delta$ as described below with respect to equations (4) and (5).

6. Theory

The following description provides a more theoretical explanation for using a standard set of data signal parameters as a generic interface for photometric devices.

More particularly, when the system is configured to eliminate polarization cross coupling effects of the sample by techniques well known in the art, the measured diffraction signals of a photometric device can be characterized using four independent signal parameters, namely the complex reflection coefficients (CRCs) $r_s$ and $r_p$. Because the absolute phase is generally of less interest and difficulty to measure, only three signal parameters are typically used. However, in practice, photometric devices typically have limited spectrum, time, and/or spatial resolutions. Thus, the measured diffraction signals include an integration of measured diffraction signals over these resolution ranges, which can result in a loss of degree of polarization (DOP). Thus, for a practical photometric device, one more signal parameter is needed to characterize the depolarization, e.g., a depolarization parameter. Thus, a total of four independent signal parameters are typically used to characterize the measured diffraction signals from photometric devices in practice.

The four independent Stokes parameters ($S_0$ $S_1$ $S_2$ $S_3$) are commonly used to characterize the polarization states of light in optical instrument. The Stokes parameters are related to the coherency matrix by the following relationship:

$$(S_0\ S_1\ S_2\ S_3) = (J_{xx} + J_{yy},\ J_{xx} - J_{yy},\ J_{xy} + J_{yx}\ i(J_{xy} - J_{yx})). \quad (1)$$

(See "Principles of Optics," M. Born and E. Wolf, Cambridge University Press, Chapter X, which is incorporated herein by reference in its entirety.)

The relationship of the Stokes parameters ($S_0$ $S_1$ $S_2$ $S_3$) to the commonly used ellipsometry parameters $\rho = \tan \Psi e^{i\Delta}$ can be expressed as:

$$(S_0\ S_1\ S_2\ S_3) = I_0 R(1 - \cos 2\Psi\ \sin 2\Psi\ \cos \Delta\ \sin 2\Psi\ \sin \Delta) \quad (2)$$

where:

$$\rho = \tan \psi e^{i\Delta} = \frac{R_p}{R_s} = \frac{E_{p0}}{E_{s0}}. \quad (3)$$

(See P. S. Hauge, R. H. Muller, and C. G. Smith, Conventions and Formulas for Using the Mueller-Stockes calculus in Ellipsometry, Surface Science, 96 (1980), 81–107, which is incorporated herein by reference in its entirety.)

For different types of photometric devices, the measured diffraction signals can be expressed as a linear combination of the 4 components of the Stokes parameter. (See "Recent Developments in Instrumentation in Ellipsometry," P. S. Hauge, IBM Tomas J. Watson Research Center, Yorktown Heights, N.Y., 10598, USA, 1979, which is incorporated herein by reference in its entirety.)

For example, unpolarized reflectometers typically characterize measured diffraction signals using one Stokes parameter, i.e., $S_0$. Polarized reflectometers typically characterize measured diffraction signals using two Stokes parameters, i.e., ($S_0$ $S_1$). Rotating polarizer ellipsometers (RPEs) typically characterize measured diffraction signals using three Stokes parameters, i.e., ($S_0$ $S_1$ $S_2$). Rotating compensator ellipsometers (RCEs) typically characterize measured diffraction signals using all four Stokes parameters, i.e., ($S_0$ $S_1$ $S_2$ $S_3$). (See "Recent Developments in Instrumentation in Ellipsometry," P. S. Hauge, IBM Tomas J. Watson Research Center, Yorktown Heights, N.Y., 10598, USA, 1979, which is incorporated herein by reference in its entirety.)

The ellipsometer parameters ($\rho = \tan \Psi e^{i\Delta}$) can be generalized using three parameters (NSC) to characterize complicated effects. In the simplest case, when there is no depolarization, this relationship can be expressed as:

$$(NSC) = (\cos 2\Psi\ \sin 2\Psi\ \sin \Delta\ \sin 2\Psi\ \cos \Delta) \quad (4)$$

$$\text{and } \sqrt{N^2 + S^2 + C^2} \equiv \beta = 1. \quad (5)$$

(See G. E. Jellison Jr., Optical materials 1 (1992), 41–47, which is incorporated herein by reference in its entirety.)

However, as noted above, photometric devices used in optical metrology of semiconductor structures typically use focused beams to produce small spot sizes (in the order of μm). Thus, for a photometric device that uses a focused beam, the measured diffraction signal is the integration of the measured diffraction signals corresponding to all the pencil rays in the effective numerical aperture (NA) of the photometric device. Each pencil ray in the NA corresponds to a specific angle of incident (AOI) and wavelength. Additionally, the square of the absolute value of the complex reflection coefficients (CRCs), $r_s$ and $r_p$, and thus the parameters (R, NSC), are functions of angle of incident (AOI), where R is the reflectivity defined below. Because of the dependence on AOI, the focusing beam is depolarized.

Thus, in general, the ellipsometer parameters ($\rho = \tan \Psi e^{i\Delta}$) are no longer sufficient to describe the characteristics of the focused beam. Additionally, in general, the definitions in equations (2)–(5) need to be reconsidered, and one can expect that the expression $\sqrt{N^2 + S^2 + C^2} \equiv \beta$ may no longer equal 1. Moreover, depolarization is not only limited by NA integration, it also can be the result of finite spectral resolution or other effects.

For an exemplary photometric device, the measured diffraction signals can be characterized by the following relationship:

$$I = PSD \cdot M \cdot PSG \quad (6)$$

where PSD is the row vector representing the response of the polarization state detector 112 to the Stokes parameters of polarized light, PSG is the column vector representing Stokes parameters of the light created by the polarization generator 106, and M is the Muller matrix. The vectors PSD and PSG are not a function of AOI and wavelength. (See G. E. Jellison Jr., Thin Solid Films 290–291 (1996), 40–45, which is incorporated herein by reference in its entirety.)

For a specific pencil ray (with given AOI and wavelength), the Muller matrix can be written as:

$$M(AOI, \lambda) = \begin{pmatrix} Rp + Rs & Rp - Rs & 0 & 0 \\ Rp - Rs & Rp + Rs & 0 & 0 \\ 0 & 0 & \text{Re}(Rsp) & \text{Im}(Rsp) \\ 0 & 0 & -\text{Im}(Rsp) & \text{Re}(Rsp) \end{pmatrix}. \quad (7)$$

where Rs,p=$|r_{s,p}|^2$, Rsp=$r_s r_p^*$ and $r_s$, $r_p$ are the complex reflection coefficients.

For a photometric device using a focused beam, the measured diffraction signals are the intensity integration of all the pencil rays over the NA and detector bandwidth around the center wavelength of the photometric device. This integration can be done solely for the Muller matrix as follows:

$$I = \int I(AOI, \lambda) d\Omega_{AOI} d\lambda = PSD \cdot \left(\int M(AOI, \lambda) d\Omega_{AOI} d\lambda\right) \cdot PSG. \quad (8)$$

Then, the generalized parameters (R, NSC) can be defined as follows:

$$R = \frac{\int (Rp + Rs)d\Omega_{AOI}d\lambda}{2\int d\Omega_{AOI}d\lambda} \quad (9)$$

$$N = -\frac{\int (Rp - Rs)d\Omega_{AOI}d\lambda}{\int (Rp + Rs)d\Omega_{AOI}d\lambda} \quad (10)$$

$$S = \frac{\int \text{Im}(Rps)d\Omega_{AOI}d\lambda}{\int (Rp + Rs)d\Omega_{AOI}d\lambda} \quad (11)$$

$$C = \frac{\int \text{Re}(Rps)d\Omega_{AOI}d\lambda}{\int (Rp + Rs)d\Omega_{AOI}d\lambda}. \quad (12)$$

The above measurement and analysis procedure of equations (8)–(12) are performed around the center wavelength of the photometric device, and the results form a spectrum of I and (R, N, S, C). The photometric device may measure the center wavelengths one at a time, or measure all center wavelengths in parallel. The generic interface and signal processing module may convert and process the measured spectra when data for a portion of the center wavelengths is available, or after the data of all center wavelengths is available.

As can be seen from above, R characterizes the change in intensity of light when reflected on a structure. More particularly, R is an average of the square of the absolute value of the complex reflection coefficients. NSC characterizes the change in polarization states of light when reflected on the structure. More particularly, N is the normalized differences between the reflectivity. S is the imaginary component, and thus the out-of-phase component, of the interference of the square of the absolute value of the complex reflection coefficients normalized to R. C is the real component, and thus the in-phase component, of the interference of the square of the absolute value of the complex reflection coefficients normalized to R.

Additionally, when a 45 degree linear polarized light is used, and thus the input Stokes parameters are $S_0=1$, $S_1=0$, $S_2=1$, and $S_3=0$, then the output stokes parameters correspond to R, NSC as $S_0=R$, $S_1=-R\times N$, $S_2=R\times C$, and $S_3=-R\times S$.

With equations (9)–(12), the normalized Muller matrix can be expressed as:

$$M' = \begin{pmatrix} 1 & -N & 0 & 0 \\ -N & 1 & 0 & 0 \\ 0 & 0 & C & S \\ 0 & 0 & -S & C \end{pmatrix}. \quad (13)$$

Thus, the measured diffraction signals can be characterized as:

$$I = PSD \cdot (RM') \cdot PSG. \quad (14)$$

Note that in general, $\overline{\sqrt{N^2+S^2+C^2}} \equiv \beta \leq 1$, and (R, NSC) are four (4) independent parameters. Additionally, note that the data signal can be separated into hardware dependent and sample dependent terms, where PSD and PSG are hardware dependent only, and R and M' are sample dependent only.

Additionally, because R and M' are not hardware dependent and the relationship between R, M' and the data signal is linear, R and M', and thus R and NSC, can be extracted from the measured diffraction signals, and can be used without detailed hardware information.

The parameters (R, NSC) can describe completely the reflection characteristics of isotropic structures, such as thin film, but they do not describe polarization cross coupling that exists in anisotropic structures, such as periodic gratings. However, using an azimuth angle of 90° eliminates the contribution of polarization cross coupling effects.

The parameters R and M', or equivalently (R, NSC), are functions of the conditions that are measured such as the center AOI, center wavelength, effective NA, spectral resolution, and the like. From the definition of the parameters R and M', or equivalently (R, NSC), these quantities can be simulated for fitting, when we have the information about AOI, center wavelength, effective NA and spectral resolution. The fitting can be done using techniques of either library-based and/or Regression-based processes.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching.

We claim:

1. An optical metrology system, comprising:
   a photometric device having:
      a source configured to generate and direct light onto a structure,
      a detector configured to detect light diffracted from the structure and to convert the detected light into a measured diffraction signal,
   a processing module configured to receive the measured diffraction signal from the detector to analyze the structure; and
   a generic interface disposed between the photometric device and the processing module configured to provide the measured diffraction signal to the processing module using a standard set of signal parameters comprising:
      a reflectance parameter that characterizes the change in intensity of light when reflected on the structure, and
      a polarization parameter that characterizes the change in polarization states of light when reflected on the structure.

2. The system of claim 1, wherein the processing module is configured to:
   compare the measured diffraction signal received from the generic interface to a first simulated diffraction signal; and
   when the difference of the measured diffraction signal and the first simulated diffraction signal is not within a matching criterion:
      generate a second simulated diffraction signal, and
      compare the measured diffraction signal to the second simulated diffraction signal.

3. The system of claim 1, wherein the structure is a thin film structure.

4. The system of claim 1, wherein the structure is a periodic grating, and wherein the photometric device is configured to use an azimuth angle of 90 degrees.

5. The system of claim 1, wherein the source generates a focused beam of light.

6. The system of claim 1, wherein the reflectance parameter is an average of the square of the absolute value of complex reflection coefficients and is an average over depolarization effects, wherein the depolarization effects include numerical aperture and spectrum bandwidth.

7. The system of claim 6, wherein the polarization parameter comprises:
a first polarization parameter that characterizes half of the difference between the square of the absolute value of the complex reflection coefficients and is an average over the depolarization effects and normalized to the reflectance parameter;
a second polarization parameter that characterizes an imaginary component of an interference of the complex reflection coefficients average over depolarization effects, and normalized to the reflectance parameter; and
a third polarization parameter that characterizes a real component of an interference of the complex reflection coefficients, average over depolarization effects, and normalized to the reflectance parameter.

8. The system of claim 7, wherein when the incident light is 45 degree linear polarized light and a first input Stokes parameter is one intensity, a second input Stokes parameter is zero, a third Stokes parameter is one intensity, and a fourth input Stokes parameter is zero, then a first output Stokes parameter is the reflectance parameter multiplied by the first input Stokes parameter, a second output Stokes parameter is negative of the first polarization parameter multiplied by the first input Stokes parameter and reflectance parameter, a third output Stokes parameter is the third polarization parameter multiplied by the first input Stokes parameter and reflectance parameter, and a fourth output Stokes parameter is negative of the second polarization parameter multiplied by the first input Stokes parameter and reflectance parameter.

9. The system of claim 1, wherein the generic interface is configured to operate with a first type of photometric device and a second type of photometric device using the standard set of signal parameters.

10. The system of claim 9, wherein the first type of photometric device is a reflectometer, and wherein the generic interface provides the measured diffraction signal received from the reflectometer using only the reflectance parameter of the standard set of signal parameters.

11. The system of claim 9, wherein the second type of photometric device is an ellipsometer, and wherein the generic interface provides the measured diffraction signal received from the ellipsometer using both the reflectance parameter and the polarization parameter of the standard set of signal parameters.

12. The system of claim 1 further comprising:
a library of simulated diffraction signals;
wherein the processing module is configured to compare the measured diffraction signal received from the generic interface to one or more simulated diffraction signals stored in the library to determine a profile of the structure.

13. The system of claim 12, wherein the library of simulated diffraction signals is indexed by one or more of the standard set of signal parameters.

14. An optical metrology system, comprising:
a processing module configured to receive a measured diffraction signal from a photometric device; and
a generic interface for the processing module configured to provide the measured diffraction signal to the processing module using a standard set of signal parameters comprising:
a reflectance parameter that characterizes the change in intensity of light when reflected on the structure wherein the reflectance parameter is an average of the square of the absolute value of complex reflection coefficients average over depolarization effects, and
a polarization parameter that characterizes the change in polarization states of light when reflected on the structure, wherein the polarization parameter comprises:
a first polarization parameter that characterizes half of the difference between the square of the absolute value of the complex reflection coefficients average over depolarization effects, and normalized to the reflectance parameter,
a second polarization parameter that characterizes an imaginary component of an interference of the complex reflection coefficients average over depolarization effects, and normalized to the reflectance parameter, and
a third polarization parameter that characterizes a real component of an interference of the complex reflection coefficients average over depolarization effects, and normalized to the reflectance parameter.

15. The system of claim 14, wherein the processing module is configured to:
compare the measured diffraction signal received from the generic interface to a first simulated diffraction signal; and
when the difference of the measured diffraction signal and the first simulated diffraction signal is not within a matching criterion:
generate a second simulated diffraction signal, and
compare the measured diffraction signal to the second simulated diffraction signal.

16. The system of claim 14 further comprising:
a library of simulated diffraction signals;
wherein the processing module is configured to compare the measured diffraction signal received from the generic interface to one or more simulated diffraction signals stored in the library to determine a profile of the structure.

17. The system of claim 16, wherein the library of simulated diffraction signals is indexed by one or more of the standard set of signal parameters.

18. A method of analyzing a structure using an optical metrology system, comprising:
directing light onto the structure to obtain a measured diffraction signal using a photometric device;
processing the measured diffraction signal using a generic interface to provide the measured diffraction signal to a processing module using a standard set of signal parameters comprising:
a reflectance parameter that characterizes the change in intensity of light when reflected on the structure, and
a polarization parameter that characterizes the change in polarization states of light when reflected on the structure; and
processing the measured diffraction signal using the processing module to analyze the structure.

19. The method of claim 18, wherein processing the measured diffraction signal comprises:
comparing the measured diffraction signal received from the generic interface to a first simulated diffraction signal; and
when the difference of the measured diffraction signal and the first simulated diffraction signal is not within a matching criterion:

generating a second simulated diffraction signal, and comparing the measured diffraction signal to the second simulated diffraction signal.

20. The method of claim 18, wherein the reflectance parameter is an average of the square of the absolute value of complex reflection coefficients average over depolarization effects.

21. The method of claim 20, wherein the polarization parameter comprises:
   a first polarization parameter that characterizes a difference between the square of the absolute value of the complex reflection coefficients average over depolarization effects, and normalized to the reflectance parameter;
   a second polarization parameter that characterizes an imaginary component of an interference of the complex reflection coefficients average over depolarization effects, and normalized to the reflectance parameter, and
   a third polarization parameter that characterizes a real component of an interference of the complex reflection coefficients average over depolarization effects, and normalized to the reflectance parameter.

22. The method of claim 18, wherein processing the measured diffraction signal comprises:
   comparing the measured diffraction signal received from the generic interface to one or more simulated diffraction signals stored in a library to determine a profile of the structure.

23. The method of claim 22, wherein the library of simulated diffraction signals is indexed by one or more of the standard set of signal parameters.

24. A computer-readable storage medium containing computer executable instructions for causing a computer to analyze a structure using an optical metrology system, comprising instructions for:
   directing light onto the structure to obtain a measured diffraction signal using a photometric device;
   processing the measured diffraction signal using a generic interface to provide the measured diffraction signal to a processing module using a standard set of signal parameters comprising:
      a reflectance parameter that characterizes the change in intensity of light when reflected on the structure, and
      a polarization parameter that characterizes the change in polarization states of light when reflected on the structure; and
   processing the measured diffraction signal using the processing module to analyze the structure.

25. The computer-readable medium of claim 24, wherein processing the measured diffraction signal comprises:
   comparing the measured diffraction signal received from the generic interface to a first simulated diffraction signal; and
   when the difference of the measured diffraction signal and the first simulated diffraction signal is not within a matching criterion:
      generating a second simulated diffraction signal, and comparing the measured diffraction signal to the second simulated diffraction signal.

26. The computer-readable medium of claim 24, wherein the reflectance parameter is an average of the square of the absolute value of complex reflection coefficients.

27. The computer-readable medium of claim 26, wherein the polarization parameter comprises:
   a first polarization parameter that characterizes half of the difference between the square of the absolute value of the complex reflection coefficients normalized to the reflectance parameter;
   a second polarization parameter that characterizes an imaginary component of an interference of the complex reflection coefficients normalized to the reflectance parameter; and
   a third polarization parameter that characterizes a real component of an interference of the complex reflection coefficients normalized to the reflectance parameter.

28. The computer-readable medium of claim 24, wherein processing the measured diffraction signal comprises:
   comparing the measured diffraction signal received from the generic interface to one or more simulated diffraction signals stored in a library to determine a profile of the structure.

29. The computer-readable medium of claim 28, wherein the library of simulated diffraction signals is indexed by one or more of the standard set of signal parameters.

* * * * *